United States Patent [19]

Sothmann et al.

[11] 4,351,825

[45] Sep. 28, 1982

[54] PROCESS FOR THE PREPARATION OF TABLETS WITH RETARDED LIBERATION OF THE ACTIVE AGENT IS PREDETERMINED

[75] Inventors: Gunnar A. Sothmann, Kirkkonummi; Esko V. Marttila, Helsinki, both of Finland

[73] Assignee: Orion-yhtymä Oy, Finland

[21] Appl. No.: 111,962

[22] Filed: Jan. 14, 1980

[30] Foreign Application Priority Data

Feb. 2, 1979 [FI] Finland ................................. 790350

[51] Int. Cl.$^3$ .......................... A61K 9/22; A61K 9/24; A61K 9/52
[52] U.S. Cl. .......................................... 424/19; 424/22
[58] Field of Search ..................................... 424/19, 22

[56] References Cited

U.S. PATENT DOCUMENTS

| | | | |
|---|---|---|---|
| 2,987,445 | 6/1961 | Levesque | 424/22 |
| 3,062,720 | 11/1962 | Costello | 424/22 |
| 3,148,124 | 9/1964 | Gaunt | 424/22 |
| 3,577,512 | 10/1968 | Shepherd et al. | 424/81 |

*Primary Examiner*—Stanley J. Friedman
*Attorney, Agent, or Firm*—Burns, Doane, Swecker & Mathis

[57] ABSTRACT

A process for the preparation of matrix-type tablets with retarded liberation of the active agent. The liberation of the active agent from the tablets takes place at a speed that has been adjusted precisely in advance. In the granulation process, polymethacrylate plastics insoluble in neutral or slightly acid water either as dissolved in an organic solvent or as a water dispersion are used as the retarding matrix substance. Before the tablets are compressed, an ester of a large-molecule fatty acid or a product obtained from same by means of hydrogenation is mixed into the grain mix in order to adjust the rate of liberation of the active agent.

3 Claims, 4 Drawing Figures

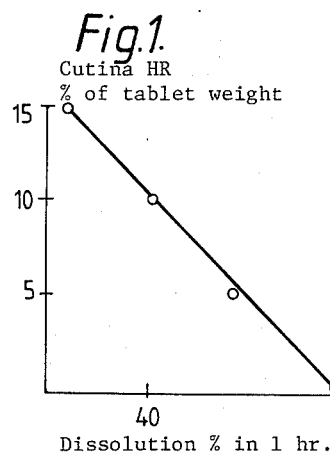
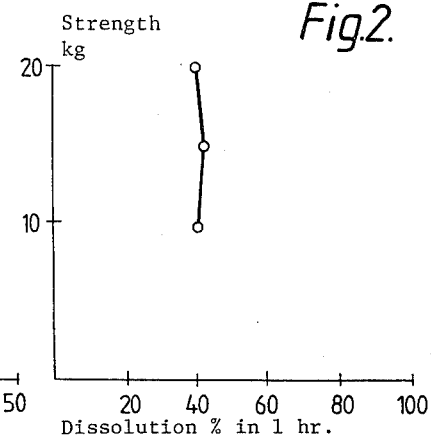
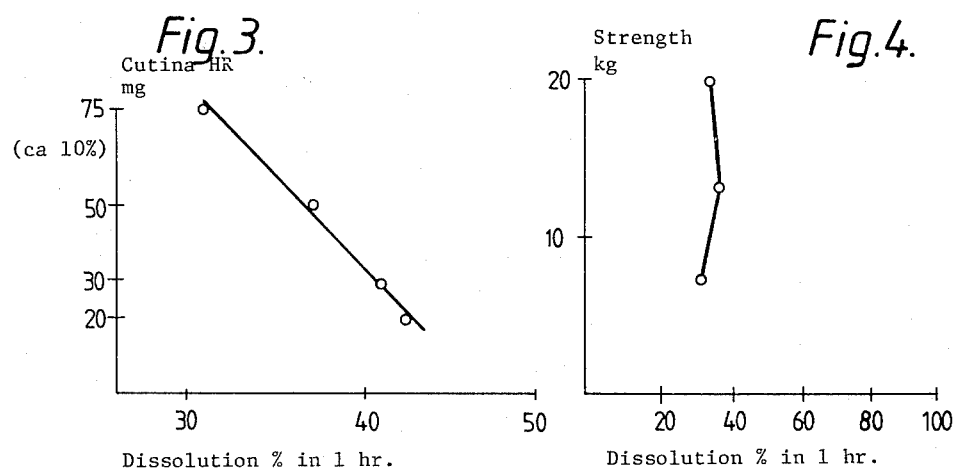
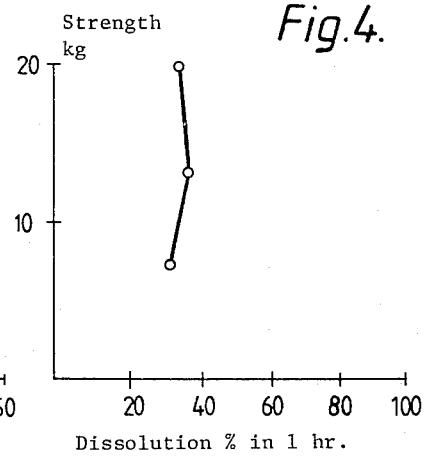

PROCESS FOR THE PREPARATION OF TABLETS WITH RETARDED LIBERATION OF THE ACTIVE AGENT IS PREDETERMINED

The subject of the present invention is a process for the preparation of such tablets in which the active agent can be made to become free from the tablet at a controlled speed and which speed of liberation can be set at the same level from batch to batch.

When a pharmaceutical substance is administered orally, it may have detrimental effects which should be avoided. The occurrence of these side effects can often be reduced by technological means by bringing the preparation into such a form from which the active agent is liberated more slowly than normally. The active agent may irritate the alimentary canal locally when high concentrations of the active agent come into contact with the intenstinal walls. In such cases, when the liberation of the active agent from the preparation is made appropriate so that its absorption and its liberation from the preparation are in a correct proportion, the irritating effect can often be avoided.

Moreover, there are cases in which the effect of the active agent is of such a short duration that the interval of administration in view of maintaining the correct concentration of active agent becomes inconveniently short, from the point of view of the patient, which again tends to cause unevenness of administration and foregetfulness about taking the medicine. Such a situation can also be made easier by means of a preparation form that has a higher quantity of active agent but retarded liberation.

There are many methods for the preparation of orally administered medicines that liberate the active agent slowly, by technological means.

It is possible to prepare grains that are coated with a film retarding the liberation of the active agent. From such grains it is possible to press the tablets, or the grains may be packed as doses into gelatin capsules. The method may also be considered as included in this group in which the entire tablet is coated with the film mentioned above.

Another main principle is that a so-called matrix tablet is prepared in which the active agent and the auxiliary agents are, together with the agent/agents retarding the liberation, pressed into a uniform network or pore structure, frame, from which the active agent is liberated slowly. Such a "network structure" can also be formed after compression, e.g., by means of heat treatment, when substances are used that melt or become softer at the temperature used.

Even though pharmaceutical preparations with retarded liberation of the active agent have proved highly important in practice, their use, however, as a rule involves the drawback that the rate of liberation of the active agent varies and may be even remarkably different in different batches of preparation. This results even in serious detrimental effects. As attempts are made, by means of slow liberation, to prevent irritation effects caused on the intestinal wall, e.g. by high local concentrations, variations in the rate of liberation may cause two types of drawbacks. If the rate of liberation is higher than intended, irritation effects cannot be eliminated adequately. On the other hand, if the rate of liberation is lower than intended, sufficiently high concentrations of active agent are not reached in the organism in order that the response to treatment should be the desired one.

When the aim of retarded liberation, e.g., longer intervals of administration or elimination of instantaneous excessively high concentrations of active agent in the organism, in these cases risks are also produced if there are variations in the liberation of the active agent. A liberation slower than intended may even cause occurrence of detrimental side effects. However, the risk may be even high if the rate of liberation becomes very high, for in preparations of this type the quantity of active agent is often larger than in ordinary tablets.

In order to amend the above drawbacks, attempts have been made to adjust the rate of liberation of the active agent to the appropriate level, e.g., by determining the compression force considered to be appropriate at the beginning of the tablet formation. This is, however, a bad way, for during the tablet production the compression force may vary out of many reasons, resulting in batch-interval variations in the rate of liberation, and these are not easy to control. Another way is to control the batches carefully afterwards and to reject the unacceptable batches. This is again an operation that involves expenses.

The process in accordance with the present invention is based on the preparation of the tablets with retarded liberation of the active agent in other respects in a way in itself known, which way is, however, before the compression step combined with the use, in accordacne with the present invention, of the additives to be descibed more closely in the following description so as to adjust the rate of liberation to the desired level.

The retard liberation of the active agent is produced by means of a so-called matrix method in which previously known polymethacrylate plastics, which have also been used for this purpose earlier, are used as formers of the retarding matrix.

The drug, i.e. the active agent, with its auxiliary agents is granulated by means of a water dispersion or a solution of a polymethacrylate insoluble in water at pH 7.0 or less, in which solution the polymer has been dissolved into organic solvents such as halogenated hydrocarbons, preferably methylenechloride, acetone, alcohols, or mixtures of same. According to studies performed, in the case of active agents highly dissociative in water, it is advantageous to use a solution of polymethacrylate in an organic solvent, because then the water dispersion tends to decompose and an effect of inhibition of dissolution is not produced with reasonably low quantities of polymer. Suitable polymethacrylate plastic is a copolymerizate of acrylic and methacrylic acid esters containing quarternary ammonium groups, or a copolymerizate of methacrylic acid and methylester of methacrylic acid with anionic character. It is also possible to use a water dispersion of a copolymerizate of methyl and ethyl esters of acrylic and methacrylic acid with neutral character.

Polymethacrylate plastics usable in the process are available, e.g., under the following trade names:
Eudragit RS
Eudragit RL
Eudragit E 30 D (30% water dispersion)
Eudragit S
Eudragit L The granulation proper may be performed by means of known processes and equipment used in the preparation of the tablet mix. The substances can then be moistened with a solution or dispersion of the polymer, screened into a grain form of appropriate size, and dried, or they may be granulated by spraying with a solution or dispersion in a so-called hover-layer apparatus or in fluidized bed apparatus.

When tablets are pressed out of such grains, it has been noticed that the liberation of the active agent from them is almost independent from the compression force, which force, as a rule, in tablets of the matrix type prepared by means of other processes, has a considerable effect on the rate of liberation. This property is important, because changes in the compression pressure occurring during the tablet formation in the production cannot produce unhomogeneity in the tablets.

In order to control the rate of liberation of the active agent to the desired level, in the process in accordance with the present invention particular controlling agents are used in the tablets pressed out of the grains produced in the way described above. When substances best suitable for this purpose were being looked for, it was noticed that a prerequisite for their usability was, besides correlation between their quantity and rate of liberation of the active agent, that the effect had already to come out when used as little quantities in order that it should be possible to avoid variations in weight and size produced by larger quantities of controlling agents in different tablet batches. The quantities used may be at the maximum 30%, preferably less than 15%, from the gross weight of the tablet. As suitable substancs were ascertained certain esters of large-molecule fatty acids which can be brought into powdery state and which either occur in nature or may be obtained from substances occurring in nature by means of hydrogenation, such as waxes and hydrogenated fats. As saturated large-molecule fatty acids can be concerned glycerides of acids of the formula $C_{11\ to\ 23}H_{23\ to\ 47}COOH$ as well as $C_{10\ to\ 30}H_{21\ to\ 61}OH$-esters of the same acids and of large-molecule alcohols. Also, it is possible to use derivatives of unsaturated fatty acids or of their hydrogenated derivatives which contain the same number of carbon atoms. Among suitable commercial products should be mentioned Cutina ® HR, which is hydrogenated castor oil, and Sterotex ®, which is hydrogenated cotton seed oil.

The controlling agents are added before compression of the tablets in the powdery form to among ready-dried grains by just stirring. Having the nature of lipids, in the spaces between the grains they control the penetration of water into the network structure of the matrix and thereby affect the rate of dissolution of the active agent. When used as suitable concentrations, the effect is in linear proportion to the quantity of the substances.

Thus, the formulation must be made to include an in each particular case appropriate quantity of a controlling agent in powdery form, whereby it is, by means of minor changes in the concentration of said agent before tablet formation, possible by means of calculation to adjust the final and precise rate of liberation of the active agent from the tablets.

An additional advantage of the use of the controlling agent in accordance with the invention is that the flow of the grains in the machine is improved and troubles of compression pressure and distribution, if any, are also eliminated along this route. It is important further that the independence of the rate of liberation of the active agent from changes in the compression pressure, mentioned above, is retained in spite of the employment of the controlling agents.

The following examples illustrate the invention more closely without, however, restricting its scope:

EXAMPLE 1

| Quinidine tablets | |
|---|---|
| Chinidin. bisulf. (anhydrous) equivalent of quinidine sulphate | 200 mg |
| Macrogol. 6000 | 20 mg |
| Talc. | 3 mg |
| Eudragit E 30 D (water dispersion) | 150 mg |
| Cutina HR | q.s. |

The quinidine bisulphate, macrogol. 6000, and the talc were mixed together. The mixture was granulated by means of Eudragit E 30 D (water dispersion), and the grains were dried.

Into the dry grain mix, the Cutina HR in powdery form was mixed. The mix was tabletted to 11 ... 12 kg (Pfizer apparatus) strength in a way in itself known.

Out of the tablets, the dissolution (liberation) of the active agent into water during 1 hour was determined as a function of the quantity of the controlling agent (Cutina HR) (FIG. 1, in the enclosed drawing).

In another experiment, the compression of the tablets was performed out of the same mix but by using different compression pressures, whereupon the dissolution of the active agent into water during 1 hour was determined as a function of the compression pressure (FIG. 2, in the enclosed drawing). As the dissolution apparatus was used the apparatus described in Pharmacopoea Nordica and in USP, and as the dissolving liquid was used water.

Analogically with the process described in example 1, the following mixtures were formed into tablets:

| | | |
|---|---|---|
| Disopyramid. phosph. | 257.6 mg | |
| Eudragit E 30 D | 110 mg | |
| Cutina HR | 10 to 40 mg | (2.6 to 9.6%) |
| Lith. sulf. cryst. | 384 mg | |
| Eudragit E 30 D | 150 mg | |
| Cutina HR | 0 to 20 mg | (0 to 3.9%) |
| Verapamil. chlorid. | 100 mg | |
| Eudragit E 30 D | 80 mg | |
| Cutina HR | 2.5 to 10 mg | (1.2 to 4.5%) |
| Perphenazin. | 8 mg | |
| Eudragit E 30 D | 30 mg | |
| Cutina HR | 0 to 10 mg | (0 to 8%) |
| Phenylpropanolamin. chlorid | 50 mg | |
| Calc. phosph. | 120 mg | |
| Eudragit E 30 D | 80 mg | |
| Cutina HR | 40 mg | (2.4%) |

It was ascertained that the dissolution was practically in direct proportion to the quantity of the Cutina HR used as the controlling agent and independent from the compression pressure.

EXAMPLE 2

| Metformine tablets | |
|---|---|
| Metformin. hydrochlorid. | 500 mg |
| Cutina HR | 50 mg |
| Eudragit RS | 70 mg |
| Methylenechlorid. | 105 mg |
| Cutina HR | q.s. |

The metformine chloride and the Cutina HR, which was used here partly already in the granulation in order to prevent adherence of the mix to the machines, were mixed together.

The mixture was moistened with Eudragit RS - methylenechloride solution and dried.

The dry mix was screened, and the Cutina HR used as the controller of liberation was mixed into the grains obtained in this way.

The dissolution of the active agent into water during 1 hour was determined from the tablets as a function of the quantity of the controlling agent (Cutina HR) (FIG. 3, in the enclosed drawing).

In the second experiment the compression of the tablets was performed from the same mixture with different compression pressures, whereupon the dissolution of the active agent during 1 hour was determined as described above (FIG. 4, in the enclosed drawing).

In an analogical way, by using methylenechloride solution of polymethacrylate, tablets of the following compositions were prepared:

| | | |
|---|---|---|
| Kal. chlorid. | 500 mg | |
| Eudragit RS | 70 mg | |
| Cutina HR | 45 mg | (6.5%) |
| Kal. chlorid. | 750 mg | |
| Eudragit RS | 100 mg | |
| Cutina HR | 30 mg | (3.1%) |
| Ferros. sulf. sicc. | 272 mg | |
| Eudragit RS | 20 mg | |
| Eudragit S 12.5 | 60 mg | |
| Cutina HR | 15 mg | (3.6%) |

And, like above, it was also in this case ascertained that the dissolution was in practically direct proportion to the quantity of the Cutina HR used as the controling agent and independent from the compression pressure.

What we claim is:

1. Process for the preparation of controlled release tablets containing an active agent comprising:
   (a) granulating the active agent with an organic solvent solution or a water dispersion of a copolymerizate of acrylic and methacrylic acid esters containing quaternary ammonium groups or an anionic copolymerizate of methacrylic acid and methyl ester of methacrylic acid;
   (b) mixing the granules with an ester of a fatty acid containing 10 to 30 carbon atoms, said ester being present in an amount less than 15% of the total weight of the mixture whereby the granules are coated with said ester; and
   (c) compressing the resulting mixture into tablets whereby the tablets release the active agent at a rate which is substantially independent of the compression pressure.

2. A process as claimed in claim 1, characterized in that a water dispersion of a copolymerizate of methyl and ethyl esters of acrylic and methacrylic acid with neutral character is used as the retarding matrix substance.

3. A process as claimed in claims 2 or 1, characterized in that the fatty acid ester is hydrogenated castor oil or hydrogenated cotton seed oil.

* * * * *